(12) United States Patent
Brusasco et al.

(10) Patent No.: US 9,199,093 B2
(45) Date of Patent: Dec. 1, 2015

(54) DEVICE AND METHOD FOR 3D DOSE TRACKING IN RADIATION THERAPY

(75) Inventors: Caterina Brusasco, Bossiere (BE); Anders Murman, Uppsala (SE)

(73) Assignee: Ion Beam Applications S.A., Louvain-la-Neuve (BE)

( * ) Notice: Subject to any disclaimer, the term of this patent is extended or adjusted under 35 U.S.C. 154(b) by 740 days.

(21) Appl. No.: 12/991,386

(22) PCT Filed: May 6, 2009
(Under 37 CFR 1.47)

(86) PCT No.: PCT/EP2009/055488
§ 371 (c)(1),
(2), (4) Date: Jun. 30, 2011

(87) PCT Pub. No.: WO2009/135881
PCT Pub. Date: Nov. 12, 2009

(65) Prior Publication Data
US 2012/0232324 A1 Sep. 13, 2012

(30) Foreign Application Priority Data
May 6, 2008 (EP) .................... 08155748

(51) Int. Cl.
*A61N 5/10* (2006.01)
(52) U.S. Cl.
CPC .......... *A61N 5/1048* (2013.01); *A61N 5/1042* (2013.01)

(58) Field of Classification Search
CPC .............. A61N 5/1048; A61N 5/1049; A61N 2005/105–2005/1063
USPC ............. 600/1, 300, 310, 407, 411, 425, 427; 378/65
See application file for complete search history.

(56) References Cited

U.S. PATENT DOCUMENTS

| | | | | |
|---|---|---|---|---|
| 6,661,870 B2 * | 12/2003 | Kapatoes et al. | ............... | 378/65 |
| 6,677,597 B1 | 1/2004 | Haberer et al. | | |
| 6,853,702 B2 | 2/2005 | Renner | | |
| 7,856,082 B2 * | 12/2010 | Flynn et al. | ............... | 378/65 |
| 7,907,987 B2 * | 3/2011 | Dempsey | ............... | 600/411 |

(Continued)

FOREIGN PATENT DOCUMENTS

| | | |
|---|---|---|
| JP | 2002522127 A | 7/2002 |
| JP | 2007526036 A | 9/2007 |

(Continued)

OTHER PUBLICATIONS

Anders Ahnesjö, "Collapsed Cone Convolution of Radiant Energy for Photon Calculation in Heterogeneous Media," Med. Phys. 16(4), 1989, pp. 577-592, 16 pages.

(Continued)

*Primary Examiner* — Jacqueline Cheng
*Assistant Examiner* — Kaylee Wilson
(74) *Attorney, Agent, or Firm* — Fitch, Even, Tabin & Flannery LLP

(57) ABSTRACT

The present invention relates to a device and method for verification of the quality of a radiation beam in conformal radiation therapy, and in particular for IMRT (Intensity Modulated Radiation Therapy) applications. The actual 3D dose distribution in the patient is tracked during the course of the entire treatment by reconstructing the photon fluences from measured 2D detector responses during irradiation in conjunction with updated patient images.

8 Claims, 6 Drawing Sheets

(56) References Cited

U.S. PATENT DOCUMENTS

| | | | |
|---|---|---|---|
| 8,160,204 | B2 | 4/2012 | Muller et al. |
| 8,218,725 | B2 | 7/2012 | Muller et al. |
| 8,716,663 | B2 * | 5/2014 | Brusasco et al. ............ 250/336.1 |
| 2007/0034812 | A1 | 2/2007 | Ma et al. |
| 2009/0116616 | A1 * | 5/2009 | Lu et al. ......................... 378/65 |
| 2010/0054413 | A1 * | 3/2010 | Sobering et al. ................ 378/65 |
| 2010/0128846 | A1 * | 5/2010 | Balakin ........................... 378/62 |
| 2010/0177872 | A1 | 7/2010 | Muller et al. |
| 2010/0215147 | A1 | 8/2010 | Muller et al. |
| 2012/0108958 | A1 | 5/2012 | Jackson |

FOREIGN PATENT DOCUMENTS

| | | |
|---|---|---|
| WO | 00/07667 A1 | 2/2000 |
| WO | WO0007667 A1 | 2/2000 |
| WO | 03/092813 A1 | 11/2003 |
| WO | 03/101538 A1 | 12/2003 |
| WO | WO2005081842 A2 | 9/2005 |
| WO | 2007/012147 A2 | 2/2007 |
| WO | 2008/006198 A1 | 1/2008 |
| WO | 2008/053026 A1 | 5/2008 |

OTHER PUBLICATIONS

Bonin et al, "A Pixel Chamber to Monitor the Beam Performances in Hadron Therapy," Nuclear Instruments and Methods in Physics Research, A 519 (2004), pp. 674-686, 13 pages.

Brusasco et al, "A Dosimetry System for Fast Measurement of 3D Depth-Dose Profiles in Charged-Particle Tumor Therapy with Scanning Techniques," Nucl. Instr. Meth. In. Phys. Res. B 168(4), Aug. 2000, pp. 578-592, 15 pages.

Frelin et al, "The DosiMap, a New 2D Scintillating Dosimeter for IMRT Quality Assurance: Characterization of Two Cerenkov Discrimination Methods," Med. Phys. vol. 35, No. 5, (2008), pp. 1651-1662, 12 pages.

Gottschalk and R. Platais, "Nuclear Interactions of 160 MeV Protons Stopping in Copper: A Test of Monte Carlo Nuclear Models," Med. Phys. 26(12), Dec. 1999, pp. 2597-2601, 5 pages.

Kapatoes et al, "A Feasible Method for Clinical Delivery Verification and Dose Reconstruction in Tomotherapy," Med. Phys, vol. 28(4), Apr. 2001, pp. 528-542, 15 pages.

Kapatoes et al, "Delivery Verification in Sequential and Helical Tomotherapy," Phys. Med. Biol, vol. 44, Jan. 1999, pp. 1815-1841, 27 pages.

Kapatoes et al, "On the Accuracy and Effectiveness of Dose Reconstruction for Tomotherapy," Phys. Med. Biol, vol. 46, Jan. 2001, pp. 943-966, 24 pages.

Kimstrand et al., "A Beam Source Model for Scanned Proton Beams." Phys. Med. Biol., vol. 52, 2007, pp. 3151-3168, 18 pages.

Lomax et al, "Intensity Modulation Methods for Proton Radiotherapy," Phys. Med. Biol. 44 (1999), pp. 185-205, 21 pages.

Lomax et al, "Treatment Planning and Verification of Proton Therapy Using Spot Scanning: Initial Experiences," Med. Phys. 31 (11), Nov. 2004, pp. 3150-3157, 8 pages.

Low et al, "A Technique for the Quantitative Evaluation of Dose Distributions," Med. Phys. 25(5), May 1998, pp. 656-661, 6 pages.

Nikos Papanikolaou, "Investigation of the Convolution Method for Polyenergetic Spectra," Med. Phys. 20 (5), 1993, pp. 1327-1336, 10 pages.

Pedroni et al., "Experimental Characterization and Physical Modelling of the Dose Distribution of Scanned Proton Pencil Beams." Phys. Med. Biol., vol. 50, 2005, pp. 541-561, 21 pages.

Timmer et al, "A Scintillating Gem for 2D-Dosimetry in Radiation Therapy," Nucl. Instr. and Methods in Physics Research Section A, vol. 478, (2002), pp. 98-103, 6 pages.

Wolfgang A. Tomé, "Beam Modeling for a Convolution/Superposition-Based Treatment Planning System," Medical Dosimetry, vol. 27, No. 1, 2002, pp. 11-19, 9 pages.

Yong Yang, "A Three-Source Model for the Calculation of Head Scatter Factors," Med. Phys. 29(9), 2002, pp. 2024-2033, 10 pages.

International Search Report, International Application No. PCT/EP2009/055484, date of completion of the report Jul. 24, 2009, 3 pages (corresponds to U.S. Appl. No. 12/991,372).

International Search Report, International Application No. PCT/EP2009/055488, date of completion of the report Jul. 16, 2009, 4 pages.

International Preliminary Report on Patentability With Written Opinion, International Application No. PCT/EP2009/055484, date of issuance of this report Nov. 9, 2010, 5 pages (corresponds to U.S. Appl. No. 12/991,372).

International Preliminary Report on Patentability With Written Opinion, International Application No. PCT/EP2009/055488, date of issuance of this report Nov. 9, 2010, 8 pages.

Extended European Search Report, European Patent Application No. 08155748.0, dated Oct. 24, 2008, 8 pages.

* cited by examiner

US 9,199,093 B2

DEVICE AND METHOD FOR 3D DOSE TRACKING IN RADIATION THERAPY

CROSS REFERENCE TO RELATED APPLICATIONS

This application is a national phase application of International Application No. PCT/EP2009/055488, filed May 6, 2009, designating the United States and claiming priority to European Patent Application No. 08155748.0, filed May 6, 2008, both of which are incorporated by reference herein in their entirety.

FIELD OF THE INVENTION

The present invention relates generally to radiation therapy used to deliver radiation doses. More particularly, the present invention relates to a device and a method for 3D dose tracking during consecutive treatment fractions.

STATE OF THE ART

In the context of the present invention, radiation therapy means treatment by X-ray or electron beams. The present invention is of particular interest for Intensity Modulated Radiation Therapy (IMRT). IMRT is a type of conformal radiation, which shapes radiation doses to closely match the shape of a target area. More particularly, IMRT is an advanced high-precision radiotherapy that utilizes computer-controlled x-ray or electron beams in order to deliver precise radiation doses to a malignant tumour or specific areas within the tumour. By the way, it can also be used to cure non malignant tumour. The radiation dose is designed to conform to the three-dimensional (3-D) shape of the tumour by modulating or controlling the intensity of the radiation beam in such a way as to focus, as much as possible, the higher radiation dose to the tumour while minimizing radiation exposure to healthy surrounding tissues. IMRT usually uses a multi leaf collimator (MLC) that can vary the radiation beam intensity of each field composing the patient treatment across the target. Therefore, the healthy surrounding tissue receives a much smaller dose of radiation than the tumour does. In addition and for special cases, there can even be a dosage that varies within the tumour. Treatment is carefully planned by using 3-D computed tomography (CT) images of the patient. Such images are used in conjunction with computerized dose calculations in order to find out the beam cross section intensity pattern that will best conform to the dose to the tumour shape. Typically, combinations of several intensity-modulated fields coming from different beam directions produce a custom tailored radiation dose that maximizes tumour dose while also protecting adjacent normal tissues. With the IMRT approach, higher and more efficient radiation doses can safely be delivered to tumours with fewer side effects compared to conventional radiotherapy techniques. Even if doses are not increased, IMRT has the potential to reduce treatment toxicity.

Treatment planning for IMRT is obviously more complex than for conventional radiation therapy, extending treatment planning time required for each patient. Unlike the conventional delivery, the complexity of the IMRT treatments makes it difficult for the operators to detect during the delivery possible deviations from the planned sequence of irradiations.

Before planning a treatment, a physical examination and medical history review is performed. This comprises CT scanning from which the radiation oncologist specifies the three-dimensional shape of the tumour and normal tissues. The dosimetrist and medical radiation physicist use this information to define the treatment plan. Several additional scanning procedures, including positron emission tomography (PET), Cone-beam CT (CBCT) and magnetic resonance imaging (MRI), might also be required for IMRT planning. These diagnostic images help the radiation oncologist to determine the precise location of the tumour target. Typically, IMRT sessions begin about a week after simulation. Typically, patients are scheduled for IMRT sessions five days a week for six to ten weeks.

The efficacy of radiation therapy relies on the accuracy of dose delivery, and, as a result, quality assurance procedures used to detect dosimetric errors are of critical importance. Examples of such procedures include measurements in order to verify the accuracy of the delivery of the planned doses calculated by treatment planning systems, and the acquisition of orthogonal portal images to ensure accurate patient positioning with respect to the treatment machine isocenter.

IMRT places even more stringent demands on these verification procedures, and makes them even more essential. The high dose gradients in IMRT fields make single point-dose measurements inadequate in verifying the significantly non uniform dose distributions. Errors in the individual IMRT beam dose distributions calculated by treatment planning systems can occur because interleaf leakage of the multi-leaf collimator (MLC) is, for example, not accurately accounted for. The potential for systematic errors in the transfer of MLC leaf sequence files from the treatment planning computer to the record and verify system, and in the mechanical accuracy of the MLC leaf movements during beam delivery further necessitates the use of accurate IMRT verification strategies.

The efficacy of radiation therapy relies also on the accuracy of positioning the target. Organs of the patient's body can shift in size, shape and position from day to day or the patient can loose weight over the period of treatment. To track the dose in the patient's anatomy during the treatment period, one can not rely on the CT images taken weeks prior to treatment and repeated patient's images need to be made during the entire treatment period.

Accordingly, there is a need to verify the accuracy of the delivered dose distribution of the treatment fields in conjunction with the actual patient's anatomy observed during the consecutive treatment fractions.

U.S. Pat. No. 6,853,702, discloses a method for treatment verification in radiation therapy. In this method, one measures the output of treatment beams over the area of the beam in a plane perpendicular to the central ray of the beam. This is accomplished by using a detector in front of the patient and one uses said measured output to calculate the dose to the patient using a dose algorithm. By referring to FIG. 1, the measured 2D detector output 10 (which corresponds to the captured images 40 of the document U.S. Pat. No. 6,853,702), is directly used to obtain the computed 3D dose 20 (corresponding to the dose distribution 58 of said document) by means of a dose algorithm and a computer program, which performs a dose computation 15. However, no means are provided to take into account the changes in the patient's anatomy occurring inbetween fractions.

It is also known from document WO 03/092813 a method for calibrating detectors to be used during treatment of a patient. This method is intended for verifying the accuracy of the delivery of a radiation treatment beam generated by a radiation apparatus to a patient. By referring to FIG. 1', this method mainly comprises two irradiation steps. During the first step, a first irradiation to a phantom (step A) is delivered and, at each time-interval, measurements (100) of the delivered dose in a phantom and information regarding the irradiation collected (200) by information means located between the source of said radiation beam and said phantom (by using for example an imaging system such as a film or EPID) are put in relationship (step B). By using this relationship it is possible to calculate calibration factors (300). According to this document, said information means may be either measurements by means of a detector or positions of Multi Leaf Collimator leaves. During a second irradiation step (step C), a patient is irradiated and once again information regarding the irradiation (400) is collected again by information means located between the source of said radiation beam and said phantom. This collected information (400) is then analysed together (D) with previous calibration factors (300) in order to obtain the total dose to the patient (500). This method therefore requires two subsequent irradiations, the first one when irradiating a phantom and a second one when irradiating a patient. It is evident that such a method is time-consuming and not accurate. Furthermore, this method never addresses to the verification of the radiation apparatus before the actual treatment of a patient. Again, no means are provided to take into account changes in patient's anatomy occurring inbetween fractions.

A delivery verification technique for tomotherapy has been described by Kapatoes J M et al. in "Delivery verification in sequential and helical tomotherapy", Phys. Med. Biol., vol. 44, 1999, 1815-1841. The technique is using a detector positioned after the patient wherein the so-called "exit detector signals" (see paragraph 2.1) are used to calculate the incident fluence distribution. As shown on FIG. 2 of this document, this detector is a so-called "exit detector" and not a transmission detector. The disadvantage of this technique is that because the detector is positioned behind the patient, the detector signals are a mixture of primary photons and scattered photons (see caption to FIG. 2). Therefore, the $D^p$ matrix must be measured after registration of the patient, before each treatment fraction. This is a very time consuming procedure.

Accordingly, no practical solution is proposed to provide an accurate radiation apparatus and dose verification method as well as to perform an easy and fast dose computation that overcomes the drawbacks above mentioned.

AIMS OF THE INVENTION

The present invention aims to provide a verification device and method that do not present the drawbacks of the state of the art.

In particular, the present invention aims to reduce the extended, time consuming machine QA and patient plan verification needed for IMRT.

Furthermore, the present invention aims to considerably enhance the state of the art method of patient specific IMRT verification, by allowing 3D dose verification in the patient's anatomical structures.

The present invention aims to track the 3D dose in the patient's anatomy during the entire course of the patient treatment using updated patient images and using 2D measurements to reconstruct the photon fluences.

SUMMARY OF THE INVENTION

According with a first aspect of the present invention a device for verification of radiation beam delivery to a patient with a radiation therapy apparatus is described. The radiation beam delivery comprises one or more treatment fractions delivered on various treatment days, said treatment fraction comprises one or more radiation beams, said radiation therapy apparatus being configurable for a given radiation beam configuration, said radiation therapy apparatus comprising an imaging system supplying updated patient images prior, during or after each treatment fraction, the device comprising:

means to receive radiation beam configurations for a given treatment fraction;

a transmission electronic 2D detector device capable of measuring 2D responses of said radiation beam in a plane perpendicular to the central axis of said radiation beam;

means to acquire in real time the 2D detector responses caused by a radiation beam delivered by said radiation therapy apparatus being configured with said radiation beam configuration;

means to import said updated patient images from said imaging system, said patient images comprising a description or image of the patient's anatomy comprising the 3D shape, density distribution and position of the target volume and/or organs at risk;

a fluence reconstructing engine, capable of computing, for each delivered radiation beam of the treatment fraction, the delivered photon fluence distribution corresponding to the delivered radiation beam, based on the measured 2D detector responses;

a dose calculation engine capable of computing the delivered 3D dose distribution within the patient based on said delivered photon fluence distribution for each radiation beam of the treatment fraction and based on imported said updated patient images;

means to visualize the said delivered 3D dose distribution in the patient's anatomy.

According to the preferred embodiment of the invention, the device further comprises:

means to store the said delivered 3D dose distribution from a single treatment fraction;

means to accumulate the delivered 3D dose distributions delivered during consecutive treatment fractions;

means to visualise the accumulated 3D dose distribution in the patient's anatomy.

Advantageously, the device according to a preferred embodiment of the present invention comprises tools to analyse the accumulated delivered 3D dose distribution. The device according to the invention further comprises:

means to analyse dose volume statistics of the accumulated 3D dose distribution based on predefined volumes or regions of interests.

More advantageously, according to this preferred embodiment of the present invention, the device further comprises:

means to importing the predicted 3D dose distribution in the patient's anatomy, said predicted 3D dose distribution being calculated with an external treatment planning system;

means to comparing the delivered 3D dose distribution with the predicted 3D dose distribution;

means to reporting a set of parameters resulting from comparison.

Advantageously, according to another preferred embodiment of the invention, the comparison of the delivered 3D dose distribution in the patient's anatomy can either be done with the initially predicted 3D dose distribution performed with an external system (e.g. treatment planning system) prior to patient treatment or the comparison can be done with an updated 3D dose distribution updated during the course of patient treatment with an external system using updated patient images taken during the course of patient treatment.

According to the preferred embodiment of the invention the device is capable of operating independently from the radiation therapy apparatus, receiving only predicted 3D dose distributions and updated patient images from external devices, optionally receiving synchronisation signals from the radiation apparatus for synchronising the 2D detector device with the radiation beam delivery.

According with a second aspect, the present invention relates to a method for verification of radiation beam delivery to a patient with a radiation therapy apparatus, said radiation beam delivery comprising one or more treatment fractions delivered on various treatment days, said treatment fraction comprising one or more radiation beams, said radiation therapy apparatus being configurable for a given radiation beam configuration, said radiation therapy apparatus comprising an imaging system supplying updated patient images obtained prior, during or after each treatment fraction. The method comprises the steps of: providing a device according to the invention; acquiring prescribed radiation beam configuration parameters; applying a treatment beam and acquiring corresponding measured 2D detector response of said treatment beam; computing the delivered photon fluence distribution corresponding to the delivered radiation beam based on the measured 2D detector responses, said delivered radiation beam being specified by said radiation beam configuration; importing updated patient images from said imaging system, said updated patient images comprising a description or image of the patient's anatomy comprising the 3D shape, density distribution and position of the target volume and/or organs at risk; computing the delivered 3D dose distribution within the patient, based on said delivered photon fluence distribution and said updated patient images; and displaying and visualizing said delivered 3D dose distribution in the patient's anatomy on a display.

DETAILED DESCRIPTION OF PREFERRED EMBODIMENTS OF THE PRESENT INVENTION

The present invention is intended to be used with a radiation therapy apparatus, which delivers high energy x-ray from an isocentric gantry linear accelerator, and especially with an IMRT apparatus wherein the beam modulation is accomplished by means of a multi leaf collimator (MLC) or by jaws.

A beam model is a mathematical description of a radiation therapy apparatus in general, which contains a number of parameters. These parameters take into account e.g. the characteristics of the accelerator (energy spectrum, lateral beam quality variations), the shapes and positions of the effective radiation sources, and the geometry and material of the beam shaping devices. A fluence computation algorithm is a set of mathematical rules which compute the fluence according to the beam model and a given parameter set. The representation of the computed fluence (units, coordinate systems) is such that it is compatible with additional computational procedures for computing deposited dose in tissue and/or detector response. Useful descriptions of basic beam modeling techniques are provided, for example, by Wolfgang A. Tomé, "Beam Modeling for a Convolution/Superposition-Based Treatment Planning System", Medical Dosimetry, Vol. 27, No. 1, pp. 11-19, 2002; or by Nikos Papanikolaou, "Investigation of the convolution method for polyenergetic spectra", Med. Phys. 20(5), 1993.

Depth dose curves and beam profiles for various depths are measured for establishing the parameters of the beam that the treatment machine can deliver. The beam model parameters are then optimised in order to give the best match between model predictions and measured dosimetric data. This beam model is then used in IMRT Treatment Planning Systems to calculate the 3-dimensional dose distribution resulting from field modulation patterns. Various strategies are used in TPSs to optimise the machine settings (numbers of fields, dose per field, field modulation, gantry angles, etc . . . ) in order to reach as close as possible the therapeutic aims.

In a preferred embodiment of the invention, a 2-dimensional transmission detector is required to provide a 2-dimensional map of measurements on a plane orthogonal to the beam direction. A technology used to realize such a detector for hadron beams is described by Bonin and al. in "A pixel chamber to monitor the beam performances in hadron therapy", Nuclear Instruments and Methods in Physics research, A 519 (2004)-674-686. This document describes a device made up of a 2-D array of 1024 ionisation chambers arranged in a regular matrix of 32×32 pixels. This technology is also used in the commercial product MatriXX manufactured by the Applicant, which has been modified for usage with photon beams by providing lateral electronic equilibrium for each chamber of the detector. The 2D detector is positioned inbetween the patient and the MLC. If measurements are performed without patient, the 2D detector can also be positioned at the patient's position.

Figure 1:
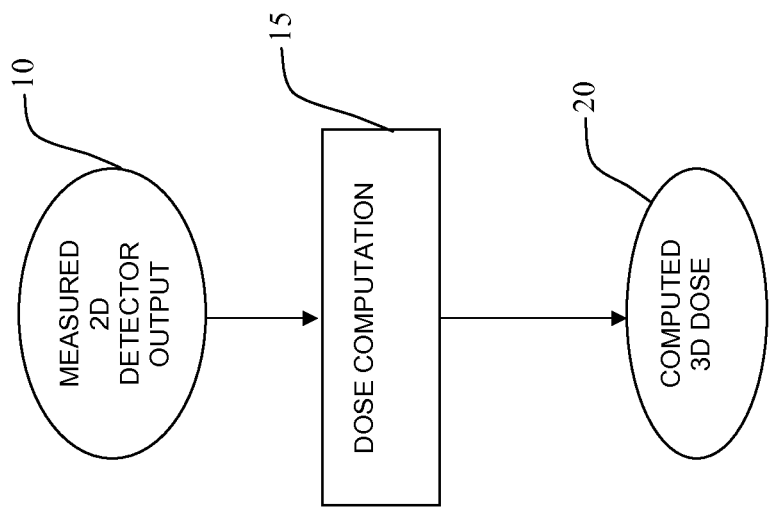
FIGS. 1 and 1' represent two methods for 3D dose computation according to the prior art.
Figure 1:
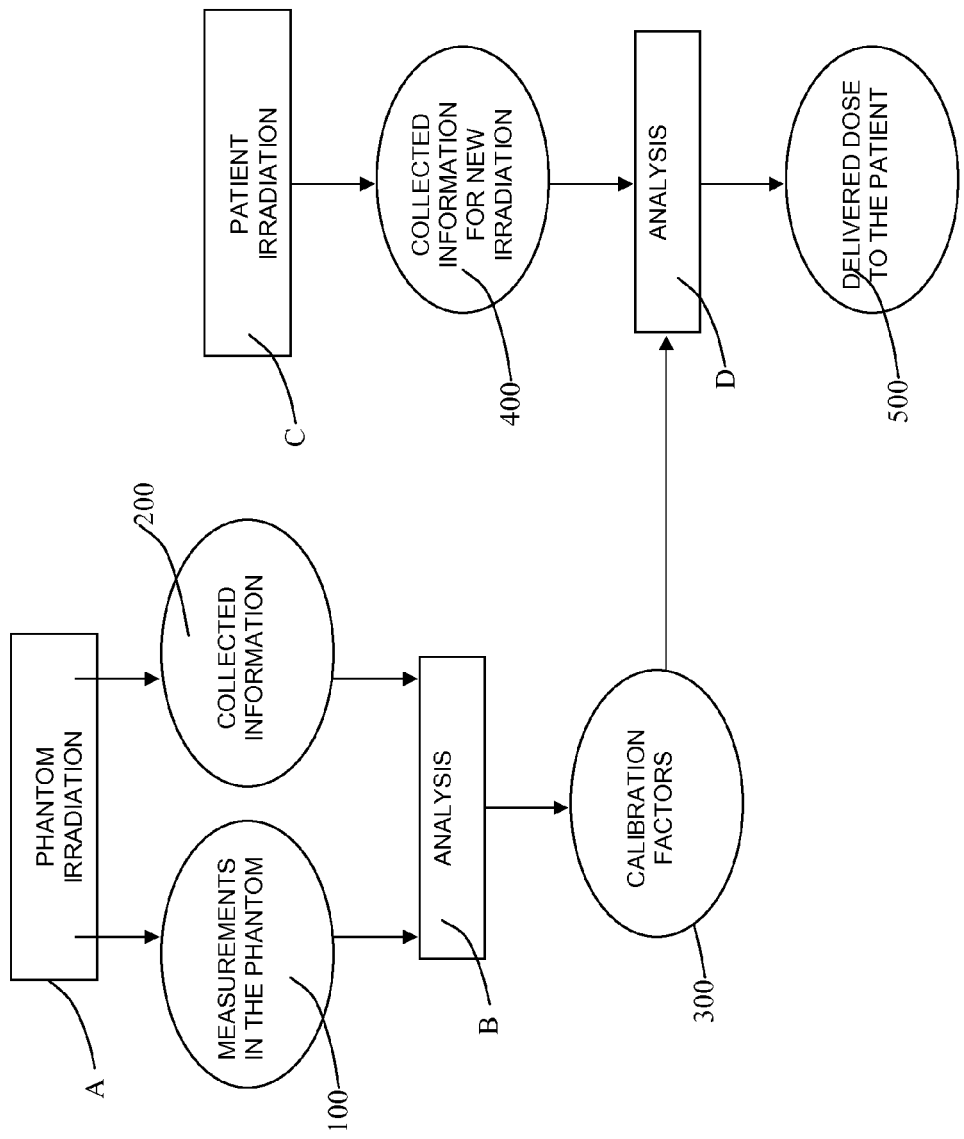
Figure 2:
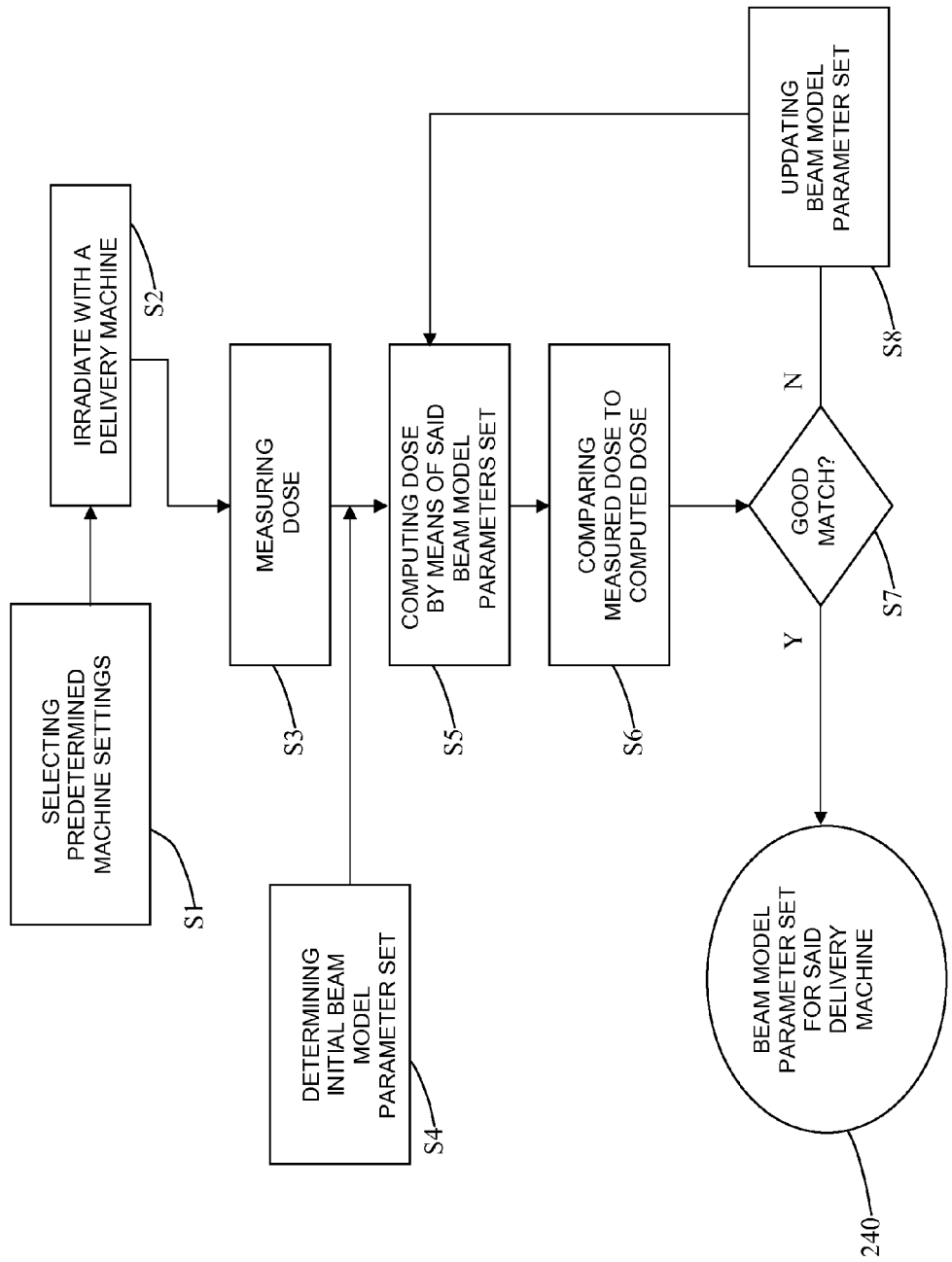
FIG. 2 is a dataflow diagram which represents the state of the art method to adapt a beam model to a given delivery machine by finding a beam model parameters set that best fits the given delivery machine.

FIG. 2 is a dataflow diagram which represents the state of the art method to adapt a beam model to a given delivery machine by finding a beam model parameters set that best fits the given delivery machine. As shown in step S1, the operator selects some predetermined machine settings. Next, as shown now in step S2 and S3, the delivery machine to be modeled is used to irradiate a phantom using said predetermined machine settings, and, by using detector means, the dose is measured. In step S4, a beam model parameters set, for a similar delivery machine, is selected and using said beam model parameters set the dose is computed in the same points as the measurements. The computed and measured doses are then compared in step S5. Should the user find the match adequate, in test S7, the current beam model parameter set 240 is said to represent the delivery machine. Otherwise, the beam model parameters set is modified, manually or automatically, as shown in step S8 and a dose computation is carried out, returning to step S5.

Figure 3:
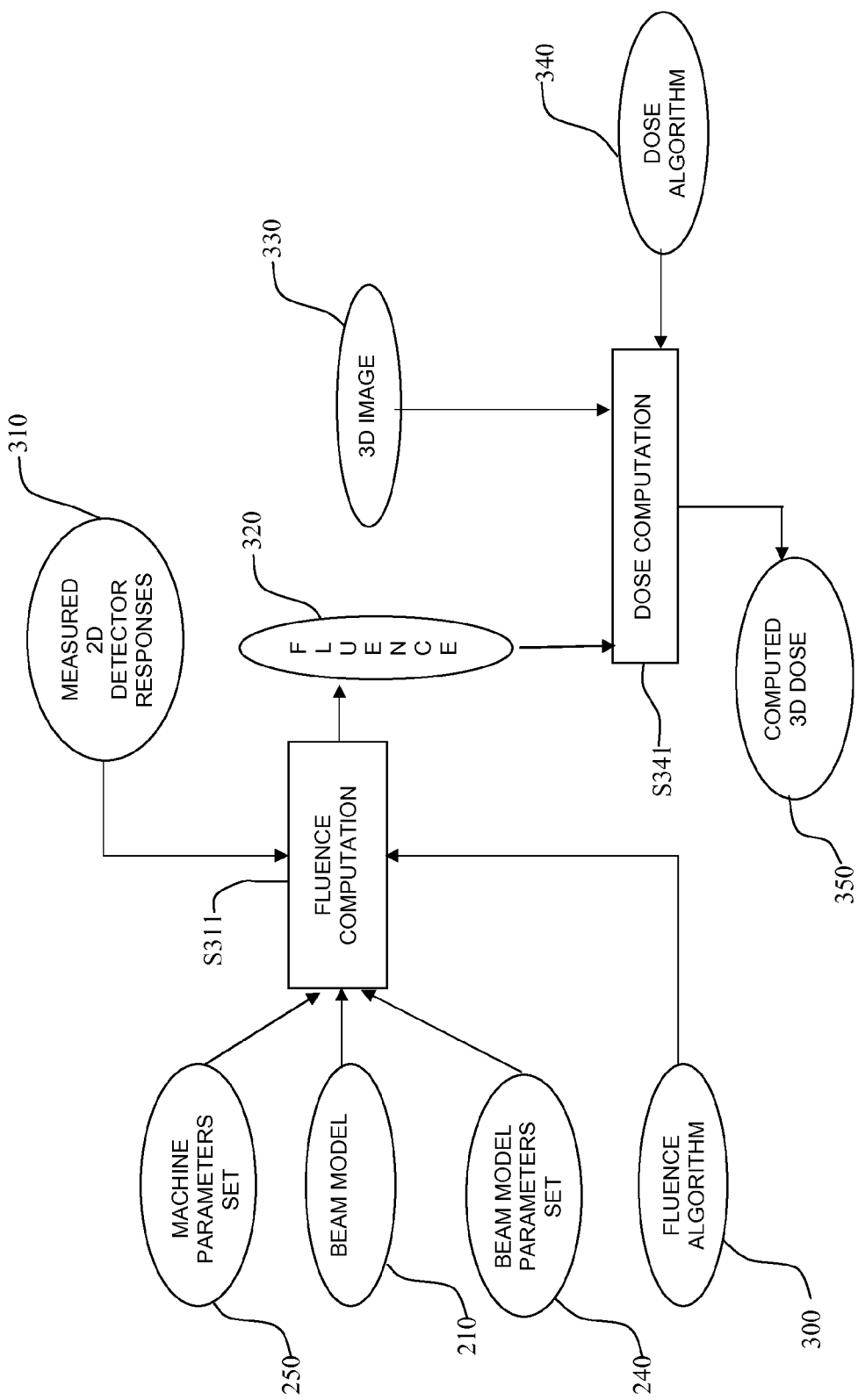
FIG. 3 is a dataflow diagram which represents a method according to the invention.

FIG. 3 is a dataflow diagram which represents a method according to the invention. Based on said beam model parameters set 240, on machine settings 250 (which are chosen according to the machine commissioning and to the settings of the treatment machine for the given radiation beam configuration provided by a Treatment Planning System (TPS) (energy and dose, dose-rate, MLC position, . . . )), on the beam model 210 of the RT apparatus, on a fluence algorithm 300 and on the measured 2D detector responses 310, one obtains, as shown in step S311, the corresponding fluence 320. An example of such a fluence algorithm is described in Yong Yang, "A three-source model for the calculation of head scatter factors", Med. Phys. 29(9), 2002.

The corresponding fluence 320 is then used together with a 3D image 330, representing a description of the target geometry and density, and a dose algorithm 340, in order to obtain the computed 3D dose 350 in the target, as shown in step S341. Such a dose algorithm is, for example, the one described by Anders Ahnesjö, "Collapsed Cone Convolution of Radiant Energy for Photon Calculation in Heterogeneous Media", Med. Phys. 16(4), 1989.

It should be noticed that by using said workflow for calculating the 3-dimensional dose distribution in said description of the target, the irradiation of a real phantom is no more required for providing a measured dose distribution in the phantom, in contrast with prior art (such as the document WO 03/092813 for example). Therefore, the irradiation step of the method is performed only once without needing any phantom or patient located in the direction of the beam.

Figure 4:
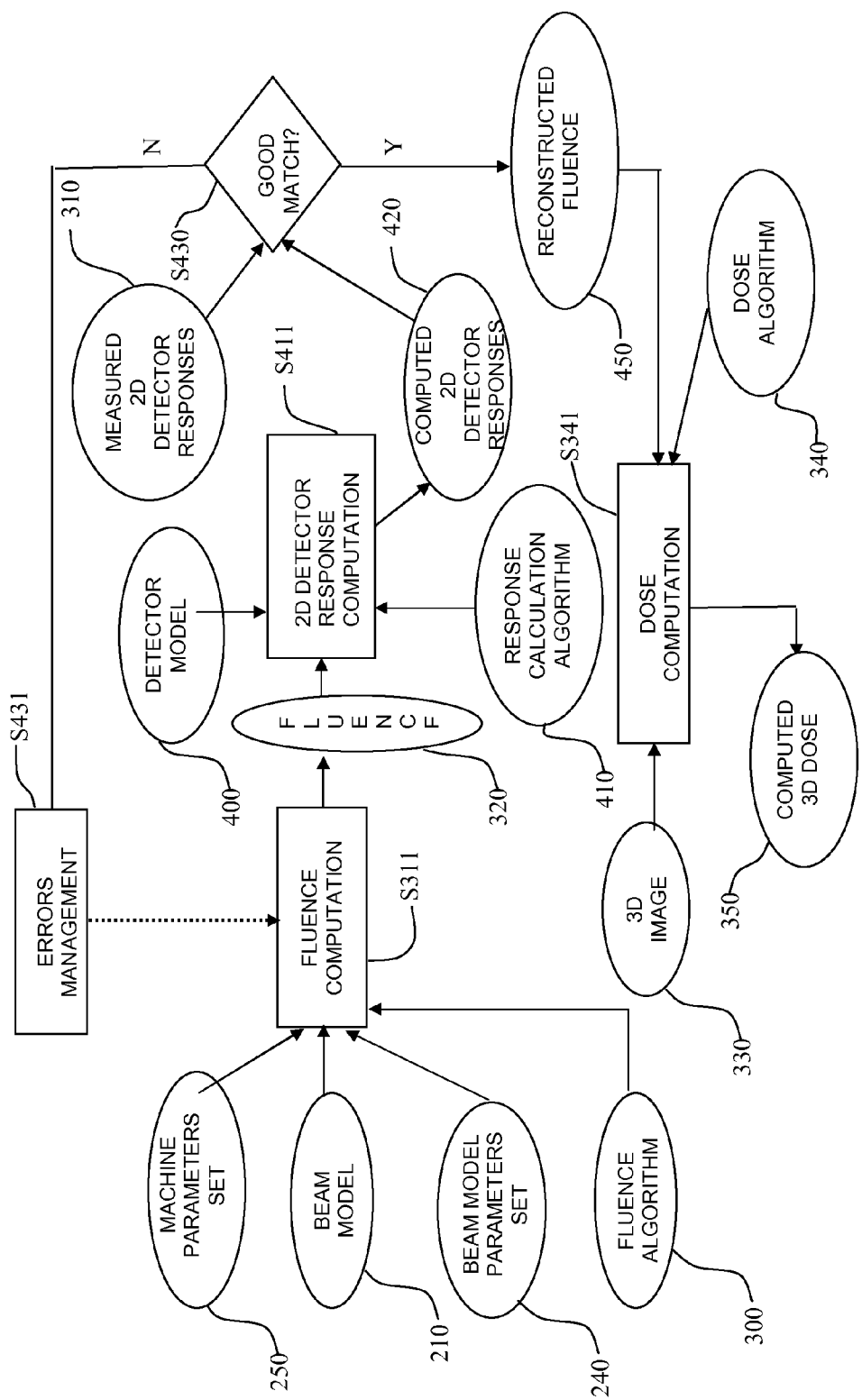
FIG. 4 is a dataflow diagram which represents another method according to the invention.

We refer now to FIG. 4. According to the invention, an optimization cycle is performed in order to provide a satisfactory computation of the fluence directed to a target. Once the corresponding fluence 320 is established as above-described, based on it one calculates the corresponding 2D detector response 420, as shown in step S411. This response calculation is based on Monte Carlo simulations of incident particles on the detector means surface, wherein all added build-up materials are also taken into account. This calculation is facilitated by a detector model 400 which describes the geometry of the device, and a response calculation algorithm 410 which describes the device response to the irradiation. The computed 2D detector response 420 is then compared to the measured 2D detector response 310 by a scoring function S430 quantifying the difference between them. In order to minimize this scoring function S430 (and thus the difference), it is possible to incorporate some delivery and/or modeling errors directly into the fluence computation (for example, by adjusting effective leaf positions, effective transmission, effective tongue-and-groove effects, effective output and effective source positions), as shown in step S431. Should this iterative modification of the fluence converge to a sufficiently small difference in the scoring function S430, it is considered that the last modified fluence 320 faithfully represents the fluence directed to the target, which is denoted as the reconstructed fluence 450. Once again, the reconstructed fluence 450 is used together with a 3D image 330 representing a description of the target geometry and density and a dose algorithm 340 in order to obtain the computed 3D dose 350 in the target.

The iterative method could also not converge, in which case there is no reconstructed fluence, but rather an indication of failure. This would typically occur if the measured response is very different from the expected one, i.e. if the wrong plan is delivered, if a segment is omitted, if significant MLC failures occur etc.

A 3D dose distribution constitutes a large data set, typically in the order of a million or more data points. Comparing two such distributions therefore requires some tools. One set of such tools comprises different types of dose volume statistics, typically based on predefined volumes (regions) of interest. The most common dose volume tool is the dose volume histogram (DVH). Another set of tools are based on extracting 2D subsets from the 3D data. The 2D subsets typically constitute planes normal to the major axes. On such planes, the dose can be represented by colour tables, isodose lines or as a 3D surface. Lines can be defined on the planes, and the dose extracted along these lines, and displayed in 2D graphs. Furthermore, point-by-point information such as the dose value and the coordinates can be obtained by selecting a point either on a plane or on a line.

When the target is an homogeneous water phantom, the comparison between the 3D delivered dose distributions with the predicted 3D dose distributions permits on the one hand to extract a report of parameters for assessing the quality of the delivery of the RT apparatus (flatness, symmetry, penumbra, field shaping, leaves position, . . . ), and on the other hand to identify possible causes of errors due to mismatches in said comparison or errors due to unexpected parameter values in said report of parameters.

Whatever is the target, however, a set of different alterations, depending on errors, can be evaluated and executed for modifying the RT apparatus configuration, i.e. the machine settings. Possible actions comprise: adjusting segment weights to compensate for output modeling errors; adjusting MLC/jaw positions to compensate for leaf tip transmission modeling errors and/or systematic positioning errors; etc.

According to the preferred embodiment of the present invention, the 3D images (330) are the updated images obtained during the course of treatment fraction delivery. Hence the device according to the present invention calculates the 3D dose distribution in the patient based on the most recent available patient images and based on the reconstructed photon fluence determined with the 2D detector responses.

Figure 5:
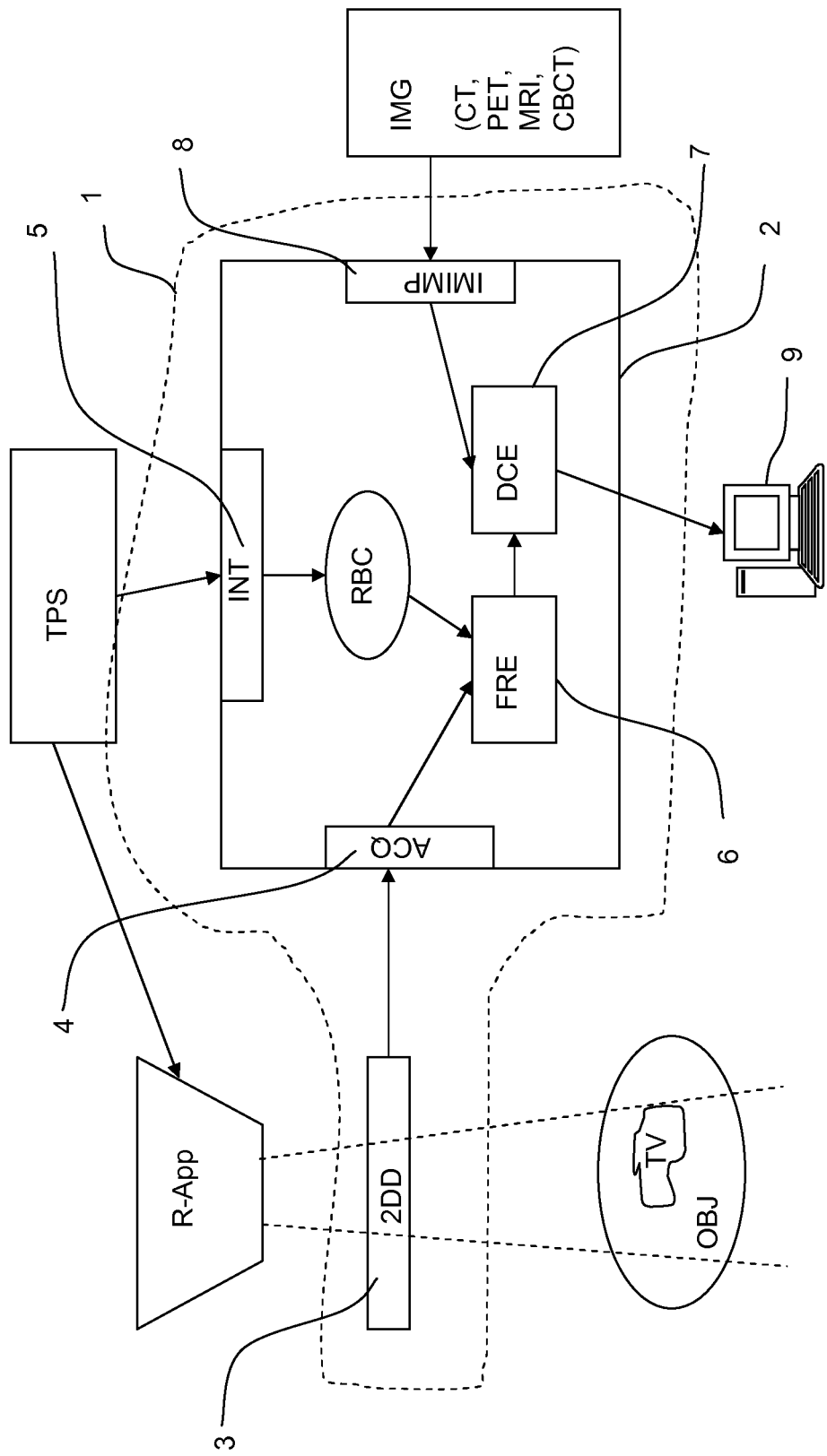
FIG. 5 is a block diagram of device for radiation therapy verification according to the invention in relation to its environment.

FIG. 5 is a device 1 for radiation therapy verification according to the invention. The device 1, (enclosed in the dashed line) comprises a master controller 2 and a 2D detector 2DD 3. The device 1 of the invention is shown in relation to the radiation therapy apparatus R-App, the treatment planning system TPS, an imaging system IMG, and the target volume TV embedded in an object OBJ. The master controller 2 of the device 1 of the invention comprises an acquisition module ACQ 4 for acquiring in real-time the signal provided by the 2D detector 2DD, and an interface INT 5 for receiving radiation beam configurations RBC from the treatment planning system TPS. Based on the acquired signals, a fluence reconstruction engine FRE 6 provides fluence data to a dose calculation engine DCE 7. The master controller 2 also comprises an image importation module IMIMP 8 for receiving images from the outside imaging system IMG such as a CT scanner, a PET scanner, an MRI imager or a CBCT (Cone-beam CT). The dose calculation engine DCE 7 computes 3D doses using the fluence data and the received images. A display device 9 shows a representation of the reconstructed 3D doses, including a 3D representation of said reconstructed 3D dose in relation to an image of the patient's anatomy. As can be seen on FIG. 5, the device 1 of the invention is totally independent of the radiation therapy apparatus R-App. It can be installed as an add-on to any existing radiation therapy apparatus R-App, without interfering with the working of said apparatus. Therefore, it provides an additional, independent security.

Accordingly, many advantages are reached by using the present invention. In fact the embodiments of the invention allow to:
  quickly identify possible sources of errors during QA and patient plan verification;
  perform a 3D dose verification in the patient's anatomy which is independent of original TPS, by using patient's anatomy data and a dose algorithm independent from the TPS;

provide the oncologist with data analysis tools in order to perform studies of protocols for given tumour entities and to compare results from different TPSs and radiation sources;

provide easy calibration procedures for MLC.

verify the delivered dose distribution directly on the patient anatomy and not only in homogeneous phantoms.

reduce global costs due to the cumbersome and long lasting state-of-art measurements and routine equipment QA tests.

The invention claimed is:

1. A device for verification of radiation beam delivery to a patient with a radiation therapy apparatus, said radiation beam delivery comprising one or more treatment fractions delivered on various treatment days, said treatment fraction comprising one or more radiation beams, said radiation therapy apparatus being configurable for a given radiation beam configuration, said radiation therapy apparatus comprising an imaging system supplying updated patient images obtained prior, during or after each treatment fraction, said device comprising:
  a receiver configured to receive radiation beam configurations for a given treatment fraction;
  a transmission electronic 2D detector device capable of measuring 2D responses of said radiation beam in a plane perpendicular to the central axis of said radiation beam, the transmission electronic 2D detector between the radiation therapy apparatus and the patient;
  a 2D detector response acquirer configured to acquire in real time the 2D detector responses caused by a radiation beam delivered by said radiation therapy apparatus being configured with said radiation beam configuration;
  an importer configured to import said updated patient images from said imaging system, said updated patient images comprising a description or image of the patient's anatomy comprising the 3D shape, density distribution and position of the target volume and/or organs at risk;
  a fluence reconstructing engine configured to compute, for each delivered radiation beam of the treatment fraction, the delivered photon fluence distribution corresponding to the delivered radiation beam based on the measured 2D detector responses, said delivered radiation beam being specified by said radiation beam configuration;
  a dose calculation engine configured to compute the delivered 3D dose distribution within the patient, said 3D dose distribution comprising the contributions from each radiation beam of the treatment fraction, computing the delivered 3D dose distribution being based on said radiation beam configuration, said delivered photon fluence distribution and said imported updated patient images;
  a display configured to display delivered 3D dose distribution in the patient's anatomy;
  a memory configured to store the said delivered 3D dose distribution from a single treatment fraction; and
  an accumulator configured to accumulate delivered 3D dose distributions delivered during consecutive treatment fractions;
  wherein the display is configured to display the accumulated 3D dose distribution in the patient's anatomy.

2. The device according to claim 1, the device further comprising:
  an analyzer configured to analyze dose volume statistics of the accumulated 3D dose distribution based on predefined volumes or regions of interests.

3. The device according to claim 1, the device further comprising:
  a further importer configured to import the predicted 3D dose distribution in the patient's anatomy, said predicted 3D dose distribution being calculated with an external treatment planning system, said 3D dose distribution comprising the contributions from each radiation beam of the treatment fraction;
  a comparer configured to compare the delivered 3D dose distribution with the predicted 3D dose distribution; and
  a reporter configured to report a set of parameters resulting from comparison.

4. The device according to claim 3, wherein said predicted 3D dose distribution is the initially planned 3D dose distribution in the patient's anatomy based on patient images initially obtained with a patient imaging system prior to the start of the treatment fraction delivery.

5. The device according to claim 3, wherein said predicted 3D dose distribution is the updated planned 3D dose distributions in the patient's anatomy based on updated patient images obtained with a patient imaging system during the course of treatment fraction delivery.

6. The device according to claim 1, said device configured to operate independently from the radiation therapy apparatus, the device configured to receive only predicted 3D dose distributions, beam configurations and updated patient images from external devices.

7. The device according to claim 1, said device configured to operate independently from the radiation therapy apparatus, the device configured to receive synchronization signals from the radiation apparatus for synchronizing the 2D detector device with the radiation beam delivery.

8. A method for verification of radiation beam delivery to a patient with a radiation therapy apparatus, said radiation beam delivery comprising one or more treatment fractions delivered on various treatment days, said treatment fraction comprising one or more radiation beams, said radiation therapy apparatus being configurable for a given radiation beam configuration, said radiation therapy apparatus comprising an imaging system supplying updated patient images obtained prior, during or after each treatment fraction, said method comprising the steps of:
  providing a device according to claim 1, wherein the transmission electronic 2D detector is placed between the radiation therapy apparatus and the patient;
  acquiring prescribed radiation beam configuration parameters;
  applying a treatment beam and acquiring corresponding measured 2D detector response of said treatment beam;
  computing the delivered photon fluence distribution corresponding to the delivered radiation beam based on the measured 2D detector responses, said delivered radiation beam being specified by said radiation beam configuration;
  importing updated patient images from said imaging system, said updated patient images comprising a description or image of the patient's anatomy comprising the 3D shape, density distribution and position of the target volume and/or organs at risk;
  computing the delivered 3D dose distribution within the patient, based on said delivered photon fluence distribution and said updated patient images; and
  displaying said delivered 3D dose distribution in the patient's anatomy on a display.

* * * * *